(12) United States Patent
Harvie

(10) Patent No.: US 11,583,382 B2
(45) Date of Patent: Feb. 21, 2023

(54) PACKAGING AND DELIVERY DEVICE FOR A BREAST IMPLANT

(71) Applicant: GC Aesthetics (Distribution) Limited

(72) Inventor: Fraser Harvie, Glasgow (GB)

(73) Assignee: GC Aesthetics (Distribution) Limited, Dublin (IE)

( * ) Notice: Subject to any disclaimer, the term of this patent is extended or adjusted under 35 U.S.C. 154(b) by 677 days.

(21) Appl. No.: 16/492,080

(22) PCT Filed: Mar. 2, 2018

(86) PCT No.: PCT/EP2018/055170
§ 371 (c)(1),
(2) Date: Sep. 6, 2019

(87) PCT Pub. No.: WO2018/162345
PCT Pub. Date: Sep. 13, 2018

(65) Prior Publication Data
US 2020/0100885 A1    Apr. 2, 2020

(30) Foreign Application Priority Data
Mar. 7, 2017 (GB) .................................... 1703631

(51) Int. Cl.
*A61F 2/12* (2006.01)
*A61F 2/00* (2006.01)

(52) U.S. Cl.
CPC .......... *A61F 2/0095* (2013.01); *A61F 2/0059* (2013.01); *A61F 2/12* (2013.01);
(Continued)

(58) Field of Classification Search
CPC ........ A61F 2/0095; A61F 2/0059; A61F 2/12; A61F 2210/0076; A61F 2230/0067; A61F 2230/0086; A61F 2250/0069; A61F 2/52
(Continued)

(56) References Cited

U.S. PATENT DOCUMENTS 3,356,090 A    12/1967 Plantinga et al.
3,755,042 A    8/1973 Robertson
(Continued)

FOREIGN PATENT DOCUMENTS

BR    1320 1201 6489 E2    10/2015
CO    7350629    8/2015
(Continued)

OTHER PUBLICATIONS

GB Search Report regarding Application No. GB1703631.0, dated Jul. 7, 2017, 3 pages.
(Continued)

*Primary Examiner* — Suzette J Gherbi
(74) *Attorney, Agent, or Firm* — Knobbe, Martens, Olson & Bear LLP

(57) ABSTRACT

Packaging for a breast implant, the packaging comprising a lid and a cavity, wherein one of the lid or the cavity is configured to provide direct delivery of the breast implant from the packaging to a surgical pocket. A method for the direct delivery of a breast implant from breast implant packaging to a surgical pocket, the method comprising the steps of: a. ensuring that a delivery device present in a lid or a cavity of the packaging is in a delivery position; b. forming an aperture in the delivery device, thereby opening the packaging; c. transferring the breast implant to the delivery device; d. positioning the delivery device in contact with the surgical pocket; and e. delivering the breast implant to the surgical pocket.

15 Claims, 6 Drawing Sheets

(52) U.S. Cl.
CPC ............... *A61F 2210/0076* (2013.01); *A61F 2230/0067* (2013.01); *A61F 2230/0086* (2013.01); *A61F 2250/0069* (2013.01); *A61F 2250/0091* (2013.01); *A61F 2250/0097* (2013.01)

(58) Field of Classification Search
USPC ........................................................ 623/7–8
See application file for complete search history.

(56) References Cited

U.S. PATENT DOCUMENTS

| | | | |
|---|---|---|---|
| 4,531,244 | A | 7/1985 | Hamas |
| 4,792,336 | A | 12/1988 | Hlavacek et al. |
| 5,500,019 | A * | 3/1996 | Johnson ............... A61B 90/02 |
| | | | 623/8 |
| 10,765,501 | B2 | 9/2020 | Van Epps et al. |
| 10,905,466 | B2 * | 2/2021 | Chacon Quiros ..... A61F 2/0095 |
| 11,234,808 | B2 * | 2/2022 | Govari ............... A61M 5/16804 |
| 2003/0036803 | A1 | 2/2003 | McGhan |
| 2006/0111777 | A1 | 5/2006 | Chen |
| 2008/0082177 | A1 | 4/2008 | Yang |
| 2009/0012372 | A1 | 1/2009 | Burnett |
| 2009/0125107 | A1 | 5/2009 | Maxwell |
| 2011/0054604 | A1 | 3/2011 | Becker |
| 2011/0082545 | A1 | 4/2011 | Freund |
| 2011/0098576 | A1 | 4/2011 | Hollstien |
| 2011/0106249 | A1 | 5/2011 | Becker |
| 2012/0041555 | A1 | 2/2012 | Manesis |
| 2012/0226352 | A1 | 9/2012 | Becker |
| 2015/0057762 | A1 | 2/2015 | Harms et al. |
| 2015/0112434 | A1 | 4/2015 | Felix et al. |
| 2015/0250582 | A1 | 9/2015 | Greenhalgh et al. |
| 2015/0351900 | A1 | 12/2015 | Glicksman |
| 2015/0359637 | A1 | 12/2015 | Miquel et al. |
| 2016/0038269 | A1 | 2/2016 | Altman et al. |
| 2016/0374720 | A1 | 12/2016 | Anderson |
| 2016/0374797 | A1 | 12/2016 | Nguyen |
| 2017/0049549 | A1 | 2/2017 | Bayat |
| 2018/0092726 | A1 | 4/2018 | Van Epps et al. |
| 2018/0110612 | A1 | 4/2018 | Schuessler et al. |
| 2019/0125401 | A1 * | 5/2019 | Chacon Quiros ......... A61F 2/12 |
| 2020/0015973 | A1 | 1/2020 | Lindsey et al. |
| 2020/0100892 | A1 | 4/2020 | Limem et al. |
| 2020/0146801 | A1 | 5/2020 | Harvie |
| 2020/0268499 | A1 | 8/2020 | Hill et al. |
| 2020/0375726 | A1 | 12/2020 | Limem et al. |
| 2021/0038367 | A1 | 2/2021 | Harvie |
| 2021/0085443 | A1 * | 3/2021 | Kocak ............... A61L 27/3691 |
| 2021/0204976 | A1 * | 7/2021 | Chacón Quirós ......... A61F 2/12 |
| 2022/0054254 | A1 * | 2/2022 | Gryskiewicz ............. A61F 2/12 |

FOREIGN PATENT DOCUMENTS

| | | |
|---|---|---|
| EP | 0370292 | 5/1990 |
| EP | 1 852 040 A1 | 11/2007 |
| EP | 2921137 | 9/2015 |
| EP | 3298962 | 3/2018 |
| WO | WO 2008/055229 | 5/2008 |
| WO | WO 2009/039373 | 3/2009 |
| WO | WO 2012/103611 A1 | 8/2012 |
| WO | WO 2012/177587 | 12/2012 |
| WO | WO 2013/122568 A1 | 8/2013 |
| WO | WO 2015/176014 | 11/2015 |

OTHER PUBLICATIONS

International Search Report and Written Opinion for Application No. PCT/EP2018/055170, dated Jun. 8, 2018, 18 pages.
"Estudio de copolimeros poli(pdioxanona) / poliglicólico"—2007 (D2 cited in Colombia).

* cited by examiner

US 11,583,382 B2

PACKAGING AND DELIVERY DEVICE FOR A BREAST IMPLANT

CROSS-REFERENCE TO RELATED APPLICATIONS

This application is a U.S. national stage application of International Patent Application No. PCT/EP2018/055170, filed Mar. 2, 2018, which claims the benefit of G.B. Application No. 1703631.0, filed Mar. 7, 2017, the disclosure of each of which is hereby incorporated by reference in its entirety.

FIELD

The invention relates to packaging for a breast implant, in particular to packaging which provides for the direct delivery of the breast implant from the packaging to a surgical pocket. The invention also relates to a packaged breast implant and to a method for the delivery of the breast implant from the packaging to a surgical pocket.

BACKGROUND

Surgical methods are continuously evolving, and a constant theme of this development is the desire to reduce incision sizes and potential for infection, such that the body suffers less trauma in surgery, reduced post-operative scarring, and secondary operations. This is a particular issue in the area of breast augmentation and reconstruction, where the long term appearance of the breast is an important consideration in determining whether the operation has been successful.

Many patients prefer pre-filled breast implants (such as silicone implants), as they can offer a more natural appearance than implants that are filled in situ. However, pre-filled implants are inevitably larger and require larger incisions, resulting in a need to develop delivery devices that can place the pre-filled breast implant in the surgical pocket through smaller and smaller incisions, yet without damage to the implant. One solution to this is the apparatus developed and sold by Keller Medical Inc. as the Keller Funnel® (described in U.S. Pat. No. 8,211,173). The Keller funnel is a tapered sleeve which is used in the manner of an icing bag, the breast implant being introduced into a larger end of the sleeve, and extruded into the surgical pocket through a smaller end of the sleeve.

However, whilst Keller sleeves have been very successful, it remains possible for the breast implant to become damaged or contaminated prior to delivery to the surgical pocket, because of the need to handle the breast implant during transfer from the sterile packaging it is received in, to the sleeve. Contamination is generally regarded as being linked to infection and capsular contracture, and to avoid this standard surgical practice is to change gloves immediately prior to handling the implant. To further reduce the likelihood of contamination, it has been suggested that pre-packaging a breast implant in a Keller Funnel® could be advantageous (US 2015/0032208). However, pre-packaging in this way may not reduce the handling required, as there is a chance that the implant would fall out of the sleeve during transit and storage. In addition, if the sleeve required activation prior to use, for instance with water or a saline solution, the implant may need to be removed from the sleeve to facilitate this. Further, packing a Keller Funnel® with a breast implant can complicate the initial product sterilisation process, as commercially available Keller Funnels® cannot be sterilised using the dry heat sterilisation methods typically used to sterilise implants. This is because the funnel is designed to deform when heated to prevent reuse. As such, the packaging of a Keller Funnel® directly with a breast implant would require either the redesign of the funnel, or adoption of an alternative sterilisation process to the cost effective dry heat sterilisation generally used for implant sterilisation.

The invention is intended to overcome or ameliorate at least some aspects of this problem.

SUMMARY

Accordingly, in a first aspect of the invention there is provided packaging for a breast implant, the packaging comprising a lid and a cavity, wherein one of the lid or the cavity is configured to provide direct delivery of the breast implant from the packaging to a surgical pocket. As used herein, "direct delivery" of the implant from the packaging to the surgical pocket, refers to delivery without the need to handle the implant. As such, direct delivery solves the contamination problem in a completely reliable way. As the packaging and the breast implant will be sterile prior to opening of the packaging, removing the need to touch the implant ensures that loss of sterility of the breast implant is minimised and therefore potential contamination.

For the avoidance of doubt, the terms "implant" and "breast implant" are used interchangeably in this document, and will generally relate to a pre-filled breast implant, such as a silicone breast implant.

It will generally be the case that the lid or the cavity is configured to provide direct delivery of the breast implant through the provision of a breast implant delivery device which is part of the lid or the cavity. This configuration, namely the provision of dual functionality packaging, offers a system where costs and stock items are reduced, as the purchase of the implant includes a component which functions initially as packaging, to ensure ongoing sterility of the implant, and at the point of use, functions as the delivery device to be used during surgery.

To reduce the volume of the packaging during transit and storage, and to provide a generally stackable product, it will generally be the case that the delivery device is movable between a folded storage position and an unfolded delivery position. In view of this, the delivery device will generally be formed from a flexible material.

It can also be of use if the delivery device is at least partially transparent or translucent. The provision of a device through which the implant can be observed allows for quality checking prior to insertion into the surgical cavity. A cost effective solution to providing for observation of the implant would be for the delivery device to be substantially transparent or translucent, subject to the presence of indicia thereon. However, it could also be the case that a window is provided in the delivery device.

Often the delivery device comprises a flexible tapered sleeve, having an open proximal end and a closed distal end, with a sleeve body there between. The device being adapted to provide for delivery of the implant from the packaging only upon opening of the distal end of the tapered sleeve. As used herein, the proximal end refers to the packaging end of the sleeve, and the distal end is the end that will generally, once opened, be inserted into the surgical pocket and through which the implant will be delivered. The use of a sleeve of this type allows for the insertion of the implant through an incision which would be too small for manual insertion and it avoids undue manipulation of the implant using the hand (undesirable because of the risk of damage to the implant and contamination). Further, as the sleeve is flexible, it can be easily folded prior to use.

Typically, prior to opening, the distal end of the sleeve will be sealed, such that the sleeve forms, for instance, a cone or pyramid. Opening of the distal end of the sleeve will often be by trimming the sleeve to remove the tip. Typically, this would be with scissors, although any sharp implement may be used as appropriate for the material from which the sleeve is formed. In this manner, the sleeve may become, for instance, frusto-conical or frusto-pyramidal.

The sleeve may be conic prior to opening, which has advantages for ease of manufacture, and strength as fewer joins are needed in the construction of the sleeve. However, it will often be the case that the sleeve is 4-sided, often pyramidal, prior to opening. A 4-sided structure (and hence a structure with a square or rectangular exit aperture) can be advantageous as the force on the sleeve at the distal end is less per surface area than for a conic sleeve of the same diameter. As a result, the force which must be applied to push the breast implant through the distal end and into the surgical cavity is less. This results in a lower level of trauma to the soft tissue of the breast cavity, and less likelihood of implant damage as it passes through the open distal end. It can be advantageous if the 4-sided structure is substantially pyramidal as this ensures that there is an even distribution of forces at the distal end, and offers a simpler construction than rectangular or irregular 4-sided structures. It would be understood that the sleeve may also have multiple sides, in any number between 3 and 10, on occasions where the sleeve is not 4-sided, 3, 5 or 6-sides may be present, as these also offer the advantages of a pyramidal structure, although where there are more than four sides manufacturing complexity is increased.

It is advantageous if the inner surface of the tapered sleeve has a low friction coefficient, as this allows the breast implant to pass more easily through the delivery device. The low friction coefficient may be achieved through the selection of a material for the delivery device which inherently has a low friction coefficient, through treatment of the inner surface of the sleeve to reduce the friction coefficient, or through the provision of a lubricant. Treatment of the inner surface of the sleeve could be through the application of a hydrophilic coating, which on contact with water generates a lubricious surface, or the application of a hydrophobic coating, which would remove the need for hydration. The hydrophilic coating may be applied using a range of techniques, often, application will be through spray coating or on-lay of the coating.

It can be advantageous for the inner surface of the tapered sleeve to be lubricated as this is an inexpensive option, allowing the materials used for the body of the sleeve to be less expensive. As noted above, it may be that the lubrication of the inner surface of the tapered sleeve is through the use of a substance which is lubricious, or a coating which becomes lubricious when activated through contact with water or a saline solution. Where contact with water or a saline solution is required, activation will be a step prior to delivery of the implant. Typically, the water or saline solution will be applied to the inner surface of the sleeve after opening, however it is possible that water or a saline solution will be present in the packaging with the implant. The lubricant will most often be an organic or synthetic oil, such as silicone oil or KY Jelly (propylene glycol combined with hydroxypropylmethyl cellulose (HPMC)). Lubricants which may be used in the subject invention include, Comfort-Coat™ (DSM), VitroStealth™ (DSM), Harmony™ (Sur-Medics), Baymedix™ CL100 (Bayer), Hydak™ T070 (Bio-Coat), iSurGlide™ (ISurTec) and Lubrilast™ (AST). These hydrophilic lubricants often comprising one or more of polyvinyl pyrrolidone, polyvinyl alcohols, propylene oxide, polyethylene oxide, polyacrylamides, poly vinyl ethers, hyaluronic acid, or combinations thereof. The lubricant may also be a cellulose based lubricant, such as a lubricant containing HMPC, or carboxymethyl cellulose. Further, polyelectrolytes may be used, such as salts of homo- and copolymers of acrylic acid, methacrylic acid, maleic acid, sulfonic acid, quaternary ammonium salts and combinations of all of the above.

Lubricants may be applied using a range of techniques, often, application will be through spray coating or on-lay of the lubricant where the lubricant is a polymer melt or solution. Vapour deposition may be used where the lubricant is a solid.

Additionally or alternatively, it can be advantageous to use a material which inherently has a low friction coefficient because this removes the need to surface treat the sleeve, or to apply or activate a lubricant. The material may be a polymeric material, such as a plastics material. For instance, polyvinylpyrrolidone (PVP), polyacrylic acid, polyethylene oxide (PEO), polysaccharides, polysiloxane, parylene and hyaluronic acid (HLA) all have inherently low friction coefficients and may be used alone or in combination.

Alternatively, treatment of the inner surface of the sleeve to reduce the friction coefficient can be advantageous, as including the step of post-treating the material expands the range of materials that may be used. It may be that for materials which are post-treated the friction coefficient can be further reduced by treatment with water or saline to activate. As such, the tapered sleeve may comprise a polymer which exhibits a reduced friction coefficient when hydrated. Materials that can have their friction coefficient reduced using this method include polyvinylpyrrolidone (PVP), polyacrylic acid, polyethylene oxide (PEO), polysaccharides, hyaluronic acid (HLA) and combinations thereof.

Surface treatment may be using techniques such as dipping, plasma coating, chemical surface modification, UV deposition, electrophoretic deposition or combinations thereof. It may be that a combination of methods may be used, for instance dipping with subsequent UV curing and plasma coating. This combination of steps is often used as this offers cost and time savings and helps to ensure the longevity of the coating. Where plasma coating is used alone, the coating has been found not to last as long as where a combination of treatments is used.

It may be that the tapered sleeve comprises a combination of two or more polymeric materials. Such a combination provides for flexibility of sleeve properties, in particular it allows for a greater control of the mechanical properties of the sleeve. It can be useful to combine polymeric materials which can expand with non-expandable materials, to provide a greater control over the implant as it exits the sleeve. An example of this combination would be silicone, for expansion, and polyamide to reinforce the sleeve. Reinforcement may be in the form of a mesh formed of the non-expandable material, bonded to the expandable material. The mesh may be evenly applied across the entire sleeve, or present at the distal end only. Further, the mesh may offer greater reinforcement at the distal end than at the proximal end.

It may be that the tapered sleeve includes one or more trimming markers. Trimming markers are indicia on the sleeve indicating where the distal end should be trimmed/cut to open. Trimming markers may be present to indicate the best position to open the sleeve for a given size and/or design of implant, in this case the trimming marker would be a delivery marker, and would indicate the most appropriate position for the open distal end during delivery. Trimming markers may also be present to indicate an appropriate point to trim the sleeve where the inner surface or lubricant is to be activated to reduce the friction coefficient. It would typically be the case that this latter marker, an activation marker, would be positioned to produce an aperture which is small relative to the open distal end as intended for delivery of the implant. This would allow saline solution or water to be added to activate the inner surface whilst minimising the risk of contamination of the implant. Contamination could be through ingress of ambient air or contact of the implant with the aperture at the distal end. By ensuring that the implant cannot come in contact with the aperture produced by the activation marker, and hence inadvertently with the external environment, this potential problem is addressed. Activation markers would only be required where the sleeve requires inner surface activation to reduce the friction coefficient to a level where the implant can slide easily through the sleeve, and where no water or saline solution is provided in the packaging.

It will often be the case that the packaging is a blister pack. Such packaging is well known and used reliably to protect and transport a wide range of products, including sterile products. Typically the lid and cavity in a blister pack are heat sealed to provide a protected environment within the packaging, and this will also typically be the case here.

Often the lid will comprise a conventional blister pack sealing material, often a material which has excellent strength and barrier properties, so that sterility during transport and storage can be relied upon. It may be advantageous to select a lid material such as high density polyethylene (HDPE), as HDPE is of high strength and has good barrier properties, ensuring that the implant remains sterile prior to use. For instance, the lid material may be Tyvek® 1073B (Dupont). Alternatively, it may be desirable to use a transparent or translucent lid material, particularly where the lid forms the delivery device. In such cases, the lid material may be selected from polyamide, polyethylene, polyethylene terephthalate and combinations thereof.

It may be the case that the cavity comprises a transparent or translucent material, such as a polymer selected from polyester, polyamide, poly(methyl methacrylate) (PMMA), polyvinyl chloride (PVC), a polyalkylene (such as polyethylene, polypropylene, and/or polybutylene), polycarbonate, polyurethane, polytetrafluoroethylene (PTFE), polyethylene terephthalate (PET), and co-polymers or combinations thereof. It will often be the case that polyamide, polycarbonate, PMMA and polyalkylenes are used as they are easy to mould, have good translucency and are generally inexpensive relative to alternative translucent or transparent polymers.

Such polymers could be rigid/or semi-rigid if the cavity is functioning purely as a blister pack, or include flexible elements if the cavity comprises the delivery device. Each of the polymers above can offer good strength and barrier properties, to ensure that sterility and package integrity are reliably maintained.

It may be that the lid and/or cavity comprise one or more resorbable or biodegradable materials, to reduce the environmental impact of the packaging. Examples of such materials include polyhydroxybuterate and polyhydroxyvalerate which may be present independently, as a blend or as a copolymer. Copolymers are generally used as they offer variations in degradation rates relative to homopolymers. Often the cavity will comprise one or more resorbable or biodegradable materials.

As noted above, the invention may be implemented in two distinct ways, wherein the lid or the cavity is configured to provide direct delivery of the breast implant from the packaging to a surgical pocket. Accordingly, the lid may comprise the delivery device, or the cavity may comprise the delivery device.

Where the lid comprises the delivery device, the lid may be a simple single layer structure, from which the delivery device is movable between a folded storage position and an unfolded delivery position. Alternatively, the cavity of the inner blister may comprise an inner lid and an outer lid, the secondary inner lid including (often entirely comprising) the delivery device. In this way, risk of damage to the delivery device during storage or transit is reduced. Further, the outer lid can be formed of a material with good strength and sterile barrier properties as described above, and the inner lid of a material specifically selected to facilitate delivery of the implant, for instance, the inner lid may be formed of a material with a low friction coefficient. Therefore, by providing a lid with two layers, each layer can be optimised for function. Where the lid comprises two layers, it will generally be the case that these are heat sealed using conventional methods to the cavity. However, the provision of a two-stage heat sealing process may be advantageous, as this would allow for the application of the inner lid, the delivery device, air evacuation, then application of the outer lid and heat sealing.

Alternatively, the cavity can comprise the delivery device. Where the cavity comprises the delivery device, the cavity may include a cavity body and a region, often distal the lid, in which the delivery device is positioned. As such the cavity may comprise, in the example of the delivery device being a tapered sleeve, a sleeve formed in one wall of the cavity. The delivery device may be formed in the cavity in an unfolded delivery position, or may be folded during storage and unfolded for delivery. Where the delivery device is formed in the cavity in an unfolded position, it may be that the cavity essentially equates to the delivery device, the cavity body being substantially absent. For instance, where the delivery device is the tapered sleeve described above, the cavity may be a tapered sleeve. In such examples, the packaging could comprise a tapered sleeve which is sealed at a proximal end with a lid material.

Where the cavity comprises the delivery device, it may be that the delivery device is formed as a separate component to the cavity body, allowing the cavity body and delivery device to be made from different materials if needed. In such cases, the cavity body and delivery device may be fixed to one another using a range of methods including heat sealing, gluing or other common means of creating an air tight seal.

According to a second aspect of the invention, there is provided a packaged breast implant, comprising packaging according to the first aspect of the invention.

In a third aspect of the invention, there is provided a method for the direct delivery of a breast implant from breast implant packaging to a surgical pocket, the method comprising the steps of:

a. ensuring that a delivery device present in a lid or a cavity of the packaging is in a delivery position;

b. forming an aperture in the delivery device, thereby opening the packaging;

c. transferring the breast implant to the delivery device;

d. positioning the delivery device in contact with the surgical pocket; and e. delivering the breast implant to the surgical pocket.

Often the step of ensuring that a delivery device is in a delivery position comprises unfolding the delivery device from a folded storage position to an unfolded delivery position. Generally this will be by simple manual actuation using the hand.

In cases where the lid comprises an inner lid and an outer lid, the inner lid including the delivery device, the method comprises the additional step of removing the outer lid prior to unfolding the delivery device. The outer lid will generally be discarded.

An aperture is then formed in the delivery device, opening the packaging. Where the delivery device is a tapered sleeve, as described above, opening will generally be by trimming the closed distal end of the tapered sleeve. The trimming may be in two stages, as described above. In cases where the inner surface of the delivery device requires activation, for instance by hydration with water (typically sterile water) or a saline solution to reduce the friction coefficient of this surface, a first cut may be made to introduce a small opening in the delivery device, to allow the introduction of water or saline solution. Once the inner surface of the delivery device has been hydrated, a second cut to allow delivery of the implant may be made. This cut will be positioned to allow for the specifically sized implant to be delivered. Accordingly, where the delivery device is a tapered sleeve, the method may comprise a step wherein the distal end of the tapered sleeve is trimmed twice, once to allow activation of an inner surface of the tapered sleeve, and once to provide a delivery aperture for the specific sized breast implant.

The implant is then transferred to the delivery device. Where the cavity includes the delivery device, transfer may be almost automatic due to the placement of the implant in the cavity during packaging. Alternatively, where either the lid or the cavity comprise the delivery device, and the delivery device has been unfolded (if necessary) transfer will generally be through simple rotation or inversion of the packaging so that the implant slides into the delivery device and is resting there. As noted above, it is a major benefit of the invention that this can be achieved without the need to directly handle the implant, and sometimes the transfer can be achieved even while the packaging remains sealed. There is therefore provided a method of direct delivery of the breast implant from the packaging to a surgical pocket (via the delivery device), without the need to handle the implant, and therefore without the risk of physical damage and contamination that direct handling will introduce.

Once the implant has been transferred to the delivery device, the lid or cavity may be discarded as appropriate to allow for ease of manipulation of the implant and delivery device. The method may therefore comprise the additional step of discarding the lid or cavity once the breast implant has been transferred to whichever of the lid or cavity includes the delivery device. When the delivery device is present in the lid, the cavity is discarded. It can be an advantage of the lid being configured to provide delivery that the cavity, generally the bulkier of the two packaging components, can be discarded.

Positioning of the delivery device in contact with the surgical pocket and delivery of the breast implant will be achieved using methods known in the art.

There is therefore optionally provided, blister pack packaging for a pre-filled breast implant, the packaging comprising a lid and a cavity, wherein the lid is configured to provide direct delivery of the breast implant from the packaging to a surgical pocket through the provision of an implant delivery device. The delivery device is generally movable between a folded storage position and an unfolded delivery position, and often at least partially transparent or translucent with one or more trimming markers. In many examples the delivery device comprises a flexible pyramidal tapered sleeve, having an open proximal end and a closed distal end, the device being adapted to provide for delivery of the implant from the packaging only upon opening of the distal end of the tapered sleeve. An inner surface of the tapered sleeve generally has a low friction coefficient achieved via a hydrophilic or hydrophobic coating, and/or the presence of a lubricant.

Also optionally provided is a method for the direct delivery of a breast implant from breast implant packaging comprising a lid and cavity to a surgical pocket, the method comprising the steps of:

a. unfolding a delivery device present in a lid of the packaging, wherein the delivery device comprises a tapered sleeve;

b. forming an aperture in the delivery device, thereby opening the packaging by trimming a distal end of the tapered sleeve;

c. transferring the breast implant to the delivery device;

d. discarding the cavity;

e. positioning the delivery device in contact with the surgical pocket; and f. delivering the breast implant to the surgical pocket.

Unless otherwise stated each of the integers described may be used in combination with any other integer as would be understood by the person skilled in the art. Further, although all aspects of the invention preferably "comprise" the features described in relation to that aspect, it is specifically envisaged that they may "consist" or "consist essentially" of those features outlined in the claims. In addition, all terms, unless specifically defined herein, are intended to be given their commonly understood meaning in the art.

Further, in the discussion of the invention, unless stated to the contrary, the disclosure of alternative values for the upper or lower limit of the permitted range of a parameter, is to be construed as an implied statement that each intermediate value of said parameter, lying between the smaller and greater of the alternatives, is itself also disclosed as a possible value for the parameter.

In addition, unless otherwise stated, all numerical values appearing in this application are to be understood as being modified by the term "about".

BRIEF DESCRIPTION OF THE DRAWINGS

In order that the invention may be more readily understood, it will be described further with reference to the figures and to the detailed description hereinafter.

DETAILED DESCRIPTION

Figure 1:
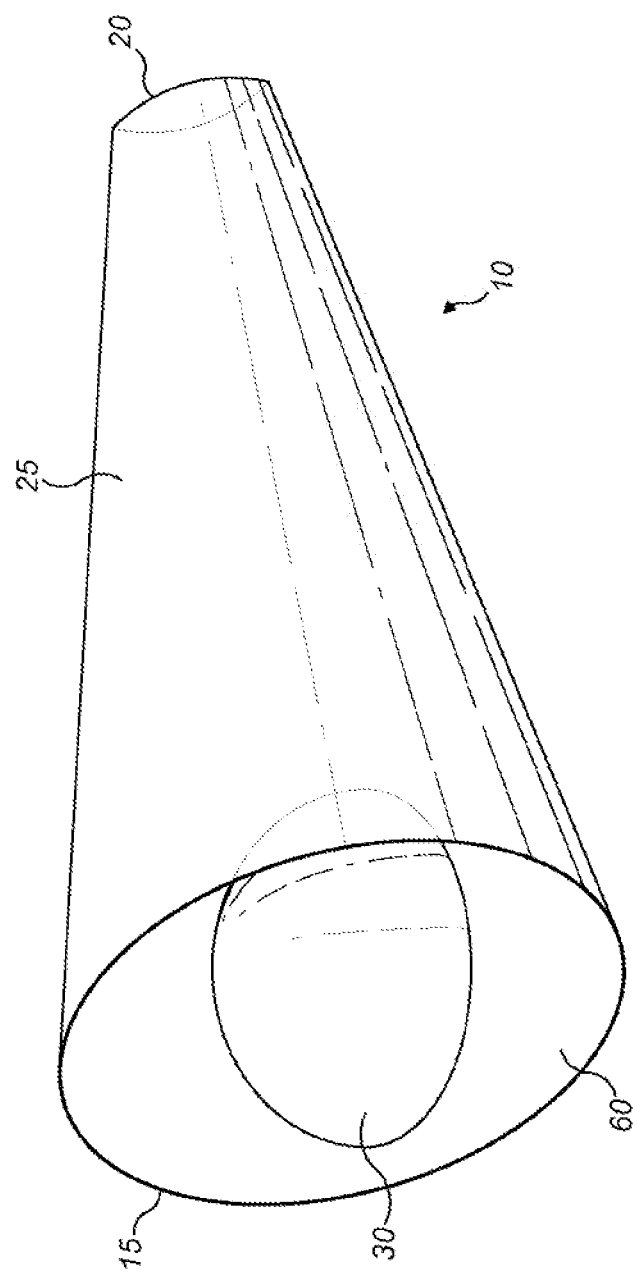
FIG. 1 shows a schematic representation of a prior art breast implant delivery device of tapered sleeve design.

FIG. 1 shows a prior art breast implant delivery device 10 of tapered sleeve design, this prior art device 10 is frusto-conical in construction with open proximal and distal ends 15, 20 and a sleeve body 25 there between housing an implant 30 in position for delivery. The distal end 20 of the delivery device 10 will be placed in a surgical pocket (not shown), and the implant 30 squeezed through the distal end 20 by manual manipulation.

Figure 2:
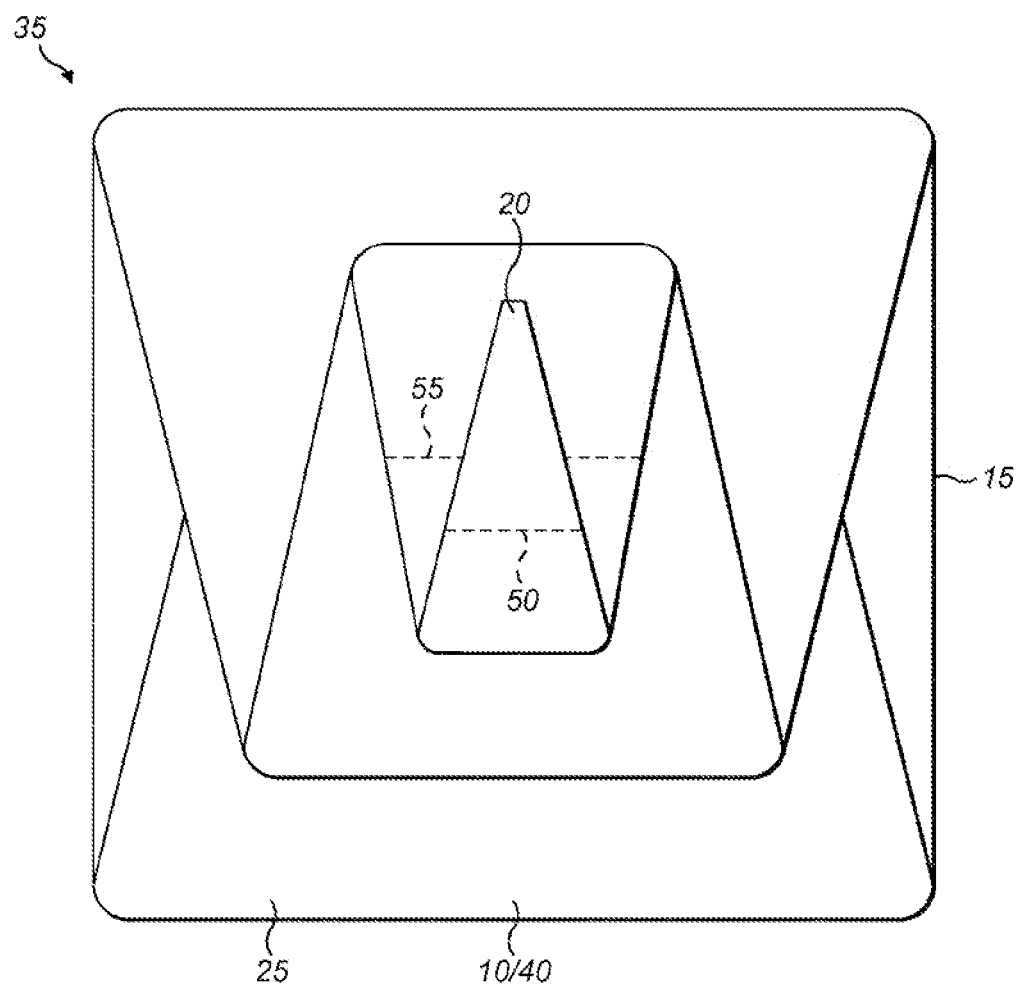
FIG. 2 shows a schematic representation of packaging wherein the lid comprises a delivery device in a folded storage position.
Figure 3:
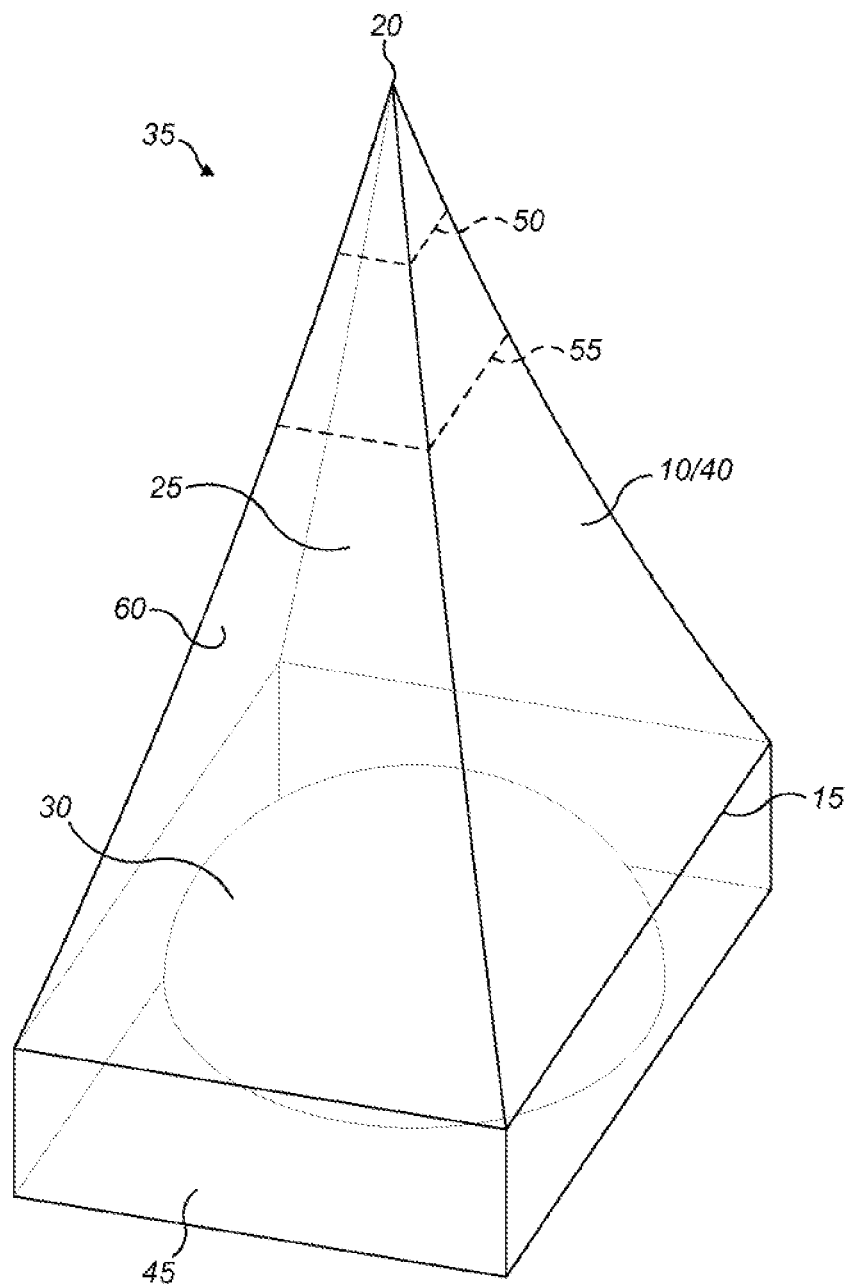
FIG. 3 shows a schematic representation of the packaging of FIG. 2 with the delivery device in an unfolded delivery position.

FIG. 2 shows packaging 35 for a breast implant 30, the packaging 25 comprising a lid 40 and a cavity (not shown). In this example, the lid 40 comprises a pyramidal tapered sleeve delivery device 10 which includes an open proximal end 15, a distal end 20 and a sleeve body 25 there between, the delivery device 10 is shown in folded configuration. The delivery device 10 includes trimming markers 50,55, specifically, an activation marker 50 and a delivery marker 55. The trimming markers 50,55 are positioned towards a distal end 20 of the delivery device 10. Cutting the sleeve at the actuation marker 50 allows for activation of the inner surface 60 of the device 10 with water or saline solution to reduce the friction coefficient of this surface 60. After activation, the open distal end 20 may be enlarged by further trimming to provide a distal end 20 aperture large enough for delivery of the implant 30 to a surgical pocket (not shown). FIG. 3 shows the packaging 35 of FIG. 2 with the delivery device 10 unfolded.

Figure 4:
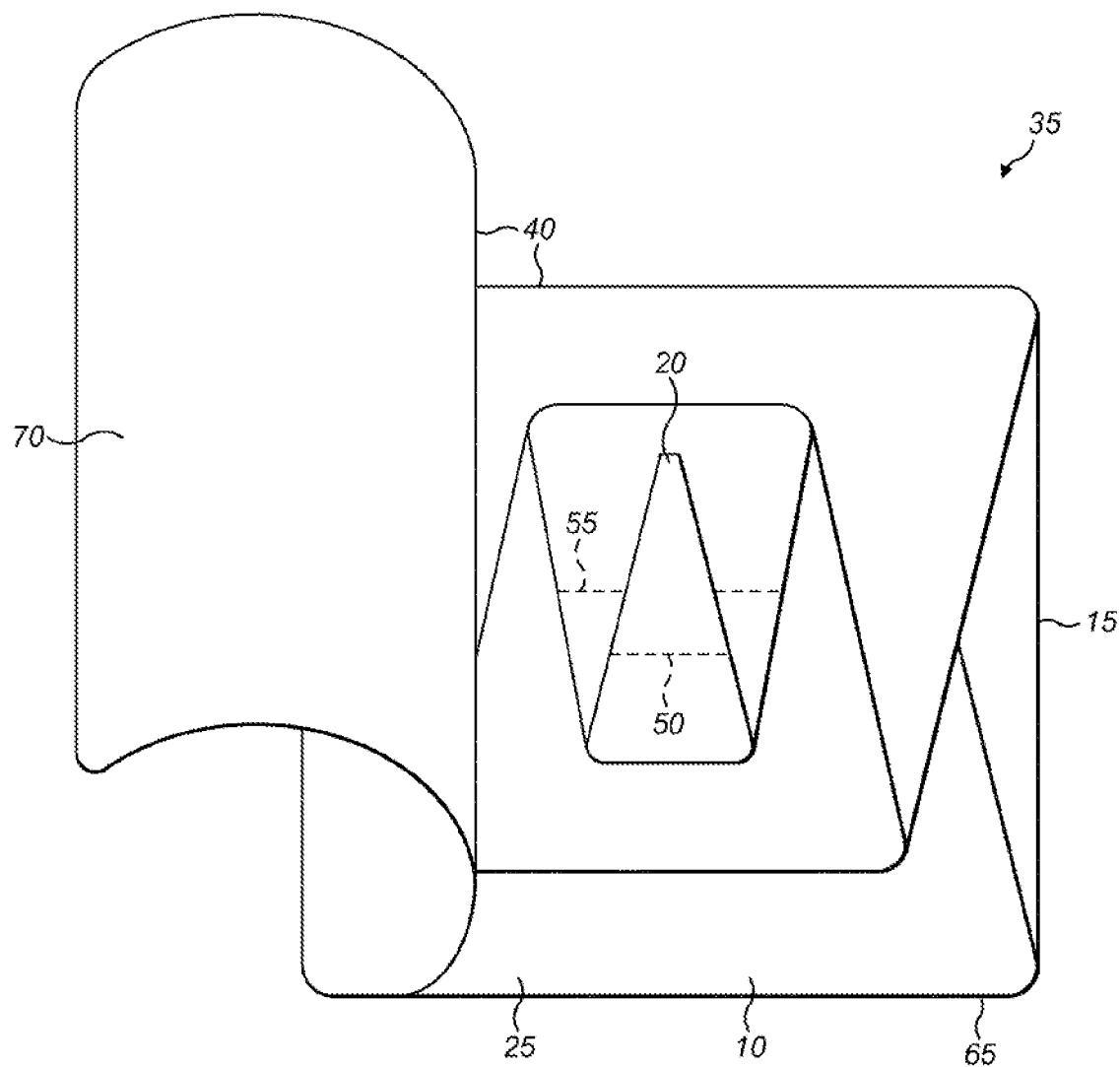
FIG. 4 shows a schematic representation of packaging wherein the lid comprises an outer layer and an inner layer which comprises a delivery device.

FIG. 4 shows an alternative example of the packaging 35, where the lid 40 has two-layers 65,70, such that the inner layer 65 is substantially as shown in FIG. 2, but an outer layer 70 is present to protect the inner layer 65. The outer layer 70 overlays the inner layer 65 during storage and transport and is removed and discarded before delivery of the implant 30.

Figure 5:
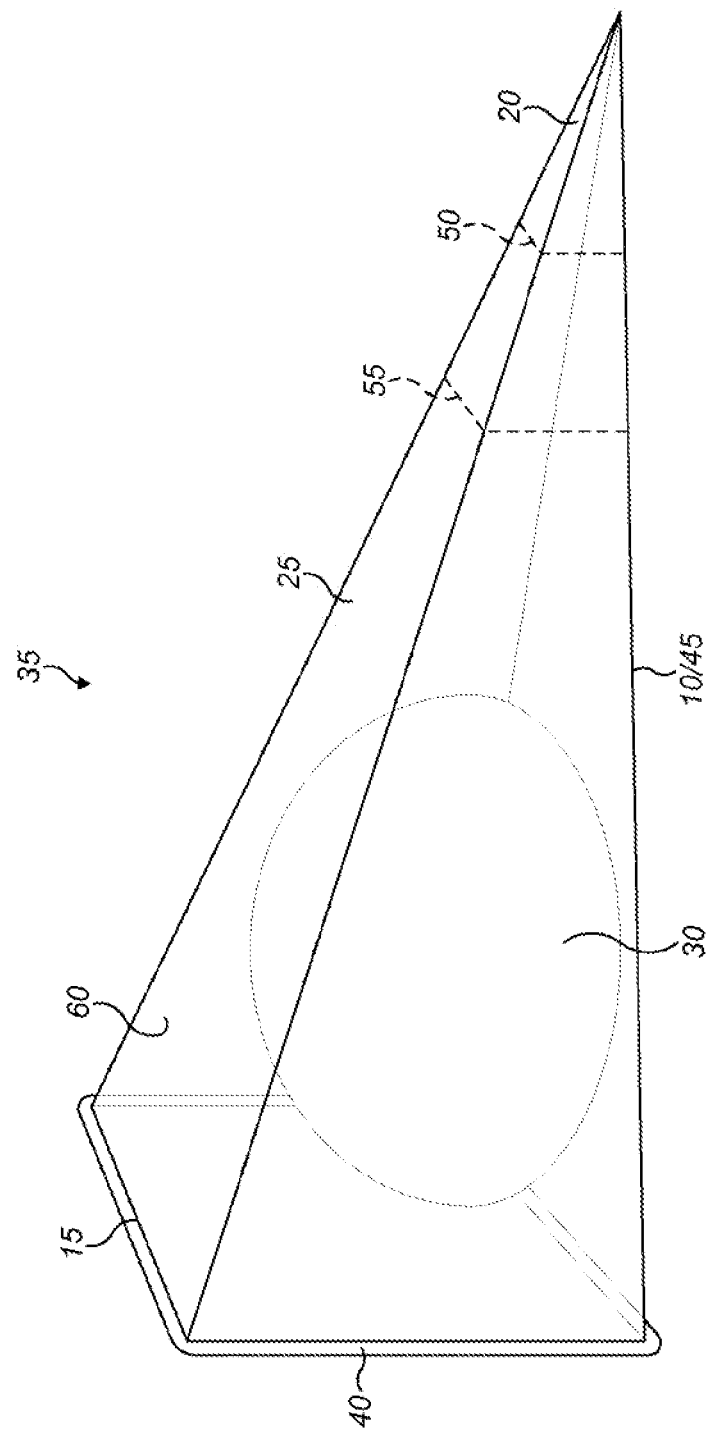
FIG. 5 shows a schematic representation of packaging wherein the cavity comprises a delivery device.

FIG. 5 shows an alternative example of the packaging 35, where the cavity 45 comprises the delivery device 10. In this example, the delivery device 10 comprises substantially all of the cavity 45, and is directly heat sealed to the lid 40.

Figure 6:
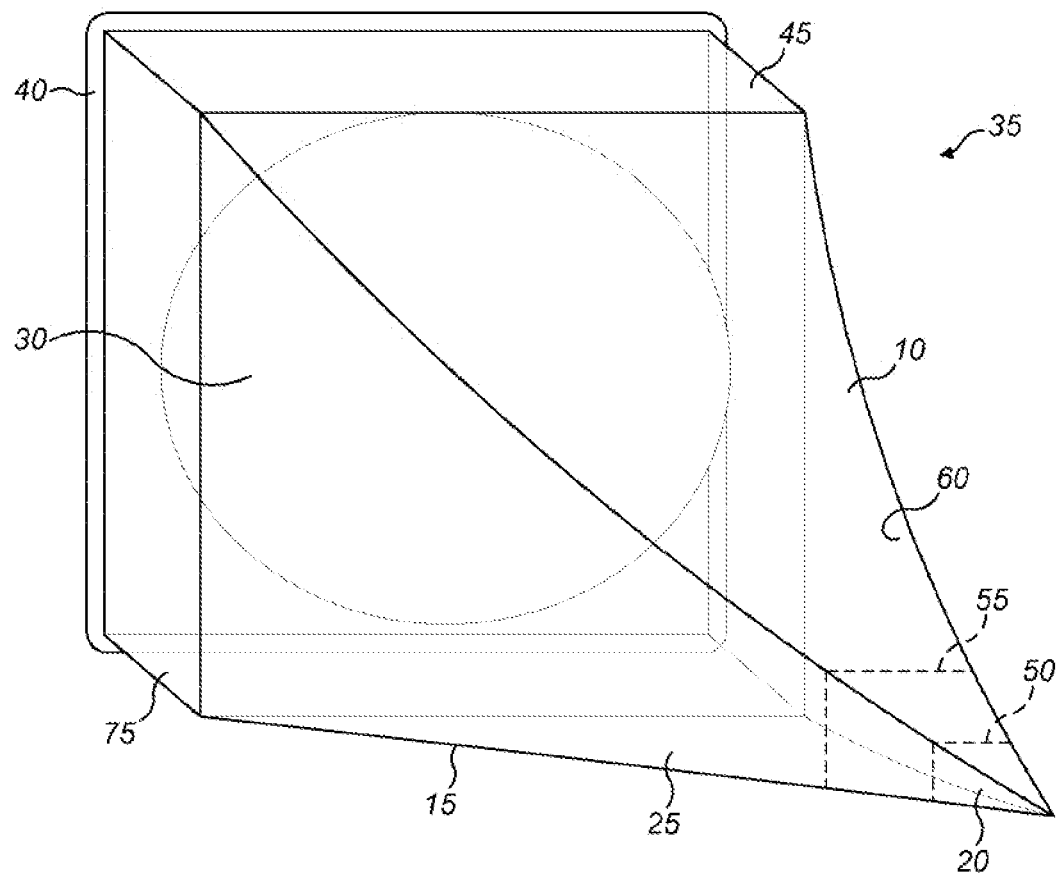
FIG. 6 shows a schematic representation of alternative packaging wherein the cavity comprises a cavity body and a delivery device.

FIG. 6 shows a further example of the packaging 35 where the cavity 45 comprises the delivery device 10. In this example the delivery device 10 is distal to the lid 40, attached to the cavity body 75.

It should be appreciated that the methods and packaging of the invention are capable of being implemented in a variety of ways, only a few of which have been illustrated and described above.

The invention claimed is:

1. A packaging for a breast implant, the packaging comprising a lid and a cavity, wherein the lid is configured to provide direct delivery of the breast implant from the packaging to a surgical pocket, and the lid or the cavity comprises a breast implant delivery device, wherein the delivery device is movable between a folded storage position and an unfolded delivery position.

2. A packaging according to claim 1, wherein the lid comprises the delivery device.

3. A packaging according to claim 2, wherein the lid comprises an inner lid and an outer lid, the inner lid including the delivery device.

4. A packaging according to claim 1, wherein the delivery device comprises a flexible tapered sleeve, having an open proximal end and a closed distal end, the device being adapted to provide for delivery of the implant from the packaging only upon opening of the distal end of the tapered sleeve.

5. A packaging according to claim 4, wherein the tapered sleeve is pyramidal.

6. A packaging according to claim 4, wherein the tapered sleeve comprises a combination of two or more polymeric materials.

7. A packaging according to claim 1, wherein the lid and the cavity comprise a blister pack.

8. A packaging according to claim 1, wherein the lid and/or cavity comprise one or more resorbable or biodegradable materials.

9. A packaged breast implant, comprising packaging according to claim 1.

10. A method for the direct delivery of a breast implant from breast implant packaging to a surgical pocket, the method comprising the steps of:
   a. ensuring that a delivery device present in a lid of the packaging is in a delivery position;
   b. forming an aperture in the delivery device, thereby opening the packaging;
   c. transferring the breast implant to the delivery device;
   d. positioning the delivery device in contact with the surgical pocket; and
   e. delivering the breast implant to the surgical pocket
   wherein the step of ensuring that a delivery device is in a delivery position comprises unfolding the delivery device.

11. A method according to claim 10, wherein the lid comprises an inner lid and an outer lid, the inner lid including the delivery device; the method comprising the additional step of removing the outer lid prior to unfolding the delivery device.

12. A method according to claim 10, wherein the delivery device comprises a flexible tapered sleeve, and wherein opening the packaging comprises trimming a distal end of the tapered sleeve.

13. A method according to claim 12, wherein the distal end of the tapered sleeve is trimmed twice, once to allow hydration of an inner surface of the tapered sleeve, and once to provide a delivery aperture for the breast implant.

14. A method according to claim 10, further comprising the additional step of discarding the lid or cavity once the breast implant has been transferred to the delivery device.

15. A packaging for a breast implant, the packaging comprising a lid providing a delivery device for direct delivery of the breast implant from the packaging device to a surgical pocket, and a cavity; wherein the lid comprises an inner lid and an outer lid, the inner lid including the delivery device.

* * * * *

UNITED STATES PATENT AND TRADEMARK OFFICE
CERTIFICATE OF CORRECTION

PATENT NO. : 11,583,382 B2
APPLICATION NO. : 16/492080
DATED : February 21, 2023
INVENTOR(S) : Fraser Harvie Page 1 of 1

It is certified that error appears in the above-identified patent and that said Letters Patent is hereby corrected as shown below:

On the Title Page

Column 1, (Applicant), Line 1: Delete "Limited" and insert -- Limited, Dublin (IE) --.

Signed and Sealed this
Twentieth Day of June, 2023

Katherine Kelly Vidal
*Director of the United States Patent and Trademark Office*